United States Patent
Yeh et al.

(10) Patent No.: US 11,571,558 B2
(45) Date of Patent: Feb. 7, 2023

(54) PRIMING DEVICE

(71) Applicant: CAREFUSION 303, INC., San Diego, CA (US)

(72) Inventors: Jonathan Yeh, Diamond Bar, CA (US); Marco Cheng, Tustin, CA (US); George Mansour, Pomona, CA (US)

(73) Assignee: CAREFUSION 303, INC., San Diego, CA (US)

( * ) Notice: Subject to any disclaimer, the term of this patent is extended or adjusted under 35 U.S.C. 154(b) by 916 days.

(21) Appl. No.: 16/265,929

(22) Filed: Feb. 1, 2019

(65) Prior Publication Data
US 2019/0167969 A1    Jun. 6, 2019

Related U.S. Application Data

(63) Continuation of application No. 14/860,478, filed on Sep. 21, 2015, now Pat. No. 10,195,415.

(51) Int. Cl.
*A61M 39/16*    (2006.01)
*A61M 39/20*    (2006.01)
(Continued)

(52) U.S. Cl.
CPC .......... *A61M 39/165* (2013.01); *A61M 5/385* (2013.01); *A61M 39/045* (2013.01);
(Continued)

(58) Field of Classification Search
CPC .. A61M 39/165; A61M 39/046; A61M 39/20; A61M 39/26; A61M 5/385;
(Continued)

(56) References Cited

U.S. PATENT DOCUMENTS

| | | | |
|---|---|---|---|
| 5,269,771 A | 12/1993 | Thomas et al. | |
| 5,330,235 A | * 7/1994 | Wagner | F16L 37/0985 285/423 |

(Continued)

FOREIGN PATENT DOCUMENTS

| | | |
|---|---|---|
| CN | 1915451 A | 2/2007 |
| CN | 102481444 | 5/2012 |

(Continued)

OTHER PUBLICATIONS

Japanese Office Action for Application No. 2018-514973, dated Aug. 12, 2020, 9 pages.

(Continued)

*Primary Examiner* — Laura A Bouchelle
*Assistant Examiner* — John A Doubrava
(74) *Attorney, Agent, or Firm* — Morgan, Lewis & Bockius LLP.

(57) ABSTRACT

Described is a priming device to prime a gas from a fluid delivery system by receiving the gas and a fluid used to push the gas into a chamber, the priming device including a housing having a chamber, an inlet port, and an opening to release gas received into the chamber. The device further includes a sleeve having an open first end for coupling with a male luer connector, a second end coupled to the housing, and an axis between the first and second ends. The sleeve defines at least one window. The device further includes an arm extending from a bottom of each window toward the first end, and a member extending radially from an inner surface of each arm. Each member has a ramp surface, an engagement surface extending transversely to the ramp surface, and an apex area that transitions between the ramp surface and the engagement surface.

13 Claims, 13 Drawing Sheets

(51) Int. Cl.
  *A61M 5/38* (2006.01)
  *A61M 39/26* (2006.01)
  *A61M 39/04* (2006.01)
  *A61M 5/14* (2006.01)
(52) U.S. Cl.
  CPC ............ *A61M 39/20* (2013.01); *A61M 39/26* (2013.01); *A61M 2005/1402* (2013.01); *A61M 2039/205* (2013.01); *A61M 2039/266* (2013.01)
(58) Field of Classification Search
  CPC .... A61M 2005/1402; A61M 2039/205; A61M 2039/266
  See application file for complete search history.

(56) References Cited

U.S. PATENT DOCUMENTS

| | | |
|---|---|---|
| 5,520,665 A | 5/1996 | Fleetwood |
| 5,676,346 A | 10/1997 | Leinsing |
| 6,299,131 B1 | 10/2001 | Ryan |
| 7,125,396 B2 | 10/2006 | Leinsing et al. |
| 7,396,051 B2 | 7/2008 | Baldwin |
| 7,766,897 B2 | 8/2010 | Ramsey et al. |
| 8,597,237 B2 | 12/2013 | Yow et al. |
| 8,808,254 B2 | 8/2014 | Lynn |
| 2003/0136932 A1 | 7/2003 | Doyle |
| 2006/0027270 A1 | 2/2006 | Truitt et al. |
| 2006/0142735 A1* | 6/2006 | Whitley ............. A61M 39/1011 604/537 |
| 2006/0157971 A1 | 7/2006 | Baldwin et al. |
| 2007/0156118 A1* | 7/2007 | Ramsey ................ A61M 39/20 604/533 |
| 2008/0287920 A1 | 11/2008 | Fangrow |
| 2011/0054440 A1 | 3/2011 | Lewis |
| 2011/0275988 A1 | 11/2011 | Davis et al. |
| 2012/0192968 A1* | 8/2012 | Bonnal ............. A61M 39/1011 137/454.2 |
| 2014/0066840 A1* | 3/2014 | Mantell ............... A61M 13/003 604/26 |
| 2014/0276651 A1 | 9/2014 | Schultz |
| 2017/0007816 A1 | 1/2017 | Mansour |

FOREIGN PATENT DOCUMENTS

| | | |
|---|---|---|
| CN | 102573953 | 7/2012 |
| CN | 102686253 A | 9/2012 |
| CN | 104203333 A | 12/2014 |
| CN | 206473659 | 9/2017 |
| EP | 0856331 A2 | 8/1998 |
| EP | 2153865 A2 | 2/2010 |
| GB | 2270725 A | 3/1994 |
| JP | H05099386 A | 4/1993 |
| JP | 2008522736 A | 7/2008 |
| JP | 2009101093 A | 5/2009 |
| JP | 2009522048 A | 6/2011 |
| JP | 2011245050 A | 12/2011 |
| JP | 5215632 | 6/2013 |
| JP | 2014030489 A | 2/2014 |
| JP | 2014132293 A | 7/2014 |
| JP | 2015119837 A | 7/2015 |
| JP | 6976932 B | 9/2018 |
| KR | 20070094538 A | 9/2007 |
| WO | WO-2006062912 A1 | 6/2006 |
| WO | WO-2013036854 A1 | 3/2013 |
| WO | WO-2014132293 A1 | 9/2014 |
| WO | WO-2014163850 A1 | 10/2014 |
| WO | WO-2015114428 | 8/2015 |
| WO | WO-2015127285 A1 | 8/2015 |

OTHER PUBLICATIONS

Australian Office Action for Application No. 2016325333, dated Apr. 17, 2020, 5 pages.
Chinese Office Action for Application No. 201610827064.8, dated Mar. 30, 2020, 18 pages.
International Search Report and Written Opinion for Application No. PCT/US2016/051146, dated Jan. 20, 2017, 16 pages.
Invitation to Pay Fees and Partial International Search Report for Application No. PCT/US2016/051146, dated Nov. 24, 2016, 6 pages.
Japanese Office Action for Application No. 2018-514973, dated May 7, 2021, 7 pages including English translation.
Australian Office Action for Application No. 2020286193, dated Mar. 3, 2022, 6 pages.
Chinese Office Action for Application No. 202011223361.4, dated Feb. 7, 2022, 26 pages including translation.
Chinese Office Action for Application No. 202011223361.4, dated Aug. 31, 2022, 7 pages including translation.
Japanese Office Action for Application No. 2021-145076, dated Aug. 26, 2022, 6 pages including translation.

* cited by examiner

PRIMING DEVICE

CROSS-REFERENCE TO RELATED APPLICATIONS

The present application is a continuation of U.S. application Ser. No. 14/860,478, titled "PRIMING DEVICE" filed Sep. 21, 2015, which issued as U.S. Pat. No. 10,195,415, on Feb. 5, 2019, the content of which is incorporated herein by reference in its entirety for all purposes.

BACKGROUND

The present disclosure relates generally to medical connectors used in fluid delivery applications. More specifically, the present disclosure relates to a priming cap configured to couple with a medical connector to prime the fluid delivery system by permitting trapped air and fluid to flow through and from the medical connector and to protect the medical connector from contamination.

Fluid delivery systems are widely used to transmit and deliver medical fluids, such as medical treatments and blood, to patients. When the fluid is delivered intravenously, it is important to release air from the fluid delivery system to prevent introduction of air into a patient's blood stream. Typically, a medical practitioner releases air trapped in the fluid delivery system by pushing a fluid in the system though an opening until the trapped air is released. After the air is released, the fluid in the system begins to be released. Once the medical fluid begins to be released, the fluid flow path is then closed.

SUMMARY

Air is released from the fluid delivery system using luer activated connectors which do not require a hypodermic needle, but instead use an activator such as a luer on the end of a syringe or IV line to create a fluid path through a valve in a connector. The removal of the connector causes the valve to close when the line is disconnected. The fluid delivery system connector must then be sanitized prior to coupling of the fluid delivery system with the patient. Sanitizing the connector aids in preventing contamination or infection of the patient's blood stream.

In some instances, such as with chemotherapy treatment, repeated contact with the medical fluid may become harmful to the medical practitioner. Therefore, it is important to retain the medical fluid bled from the system in a container, thereby preventing exposure to the medical fluid.

An aspect of the present disclosure provides a priming device comprising: a housing defining a chamber and an inlet port, wherein the chamber and the inlet port are fluidly coupled, the housing comprising: an opening extending from within the chamber to outside the housing and configured to permit a gas to exit the chamber; a valve extending from the inlet port toward the chamber, wherein in a sealed position the valve seals the inlet port, and in an open position, the valve does not seal the inlet port; and a cover body having an open first end, an open second end, and an axis between the first end and the second end, the first end configured to couple with a male luer connector, the second end configured to couple with the inlet port of the housing.

Some embodiments provide when the priming device is in a priming-ready configuration, the inlet port is disposed within the second end of the cover body, and the valve is in a sealed position. Certain aspects provide when the priming device is in a priming configuration, the inlet port is advanced over a portion of a male luer connector stem to fluidly couple the housing with the male luer connector, thereby opening the valve and creating a fluid pathway between the male luer connector and the chamber. Some aspects provide when the priming device is in a post-priming configuration, the housing is decoupled from the cover body, the cover body remaining coupled to the male luer connector.

In certain instances of the present disclosure, the cover body comprises one or more protrusion extending axially inward from an inner surface of the cover body, the protrusion having an inner surface defining an inner cross-sectional width. In some embodiments, the protrusion is one more or tabs. In some instances, the first end of the cover body comprises an inner cross-sectional width configured to receive an outer surface of the male luer connector.

Some embodiments of the present disclosure provide a lid coupled to the second end of the cover body by a hinge, the lid configured to seal the second end of the cover body when the housing is decoupled from the cover body. In some embodiments, a hydrophobic filter is disposed in the opening. According to certain implementations of the present disclosure, the housing comprising a passage formed between the inlet port and a chamber inlet, the chamber inlet separating the passage from the chamber. In some instances, the chamber inlet comprises a lumen extending toward the inlet port fluidly connecting the chamber and the passage.

According to certain implementations of the present disclosure, a thread extends circumferentially outward from the inlet port, the thread being located between the male luer connector and the second end in the priming-ready and priming configurations. In some implementations, the thread comprises an outer cross-sectional width that is greater than the inner cross-sectional width of a protrusion extending axially inward from an inner surface of the cover body.

An aspect of the present disclosure provides a priming device comprising: a housing defining a chamber and an inlet port, wherein the chamber and the inlet port are fluidly coupled, the housing comprising: an opening extending from within the chamber to outside the housing and configured to permit a gas to exit the chamber; a sleeve having an open first end configured to couple with a male luer connector, a second end coupled to the housing, and an axis between the first end and the second end, wherein the sleeve defines at least one window; an arm extending from a bottom of each window toward the first end; and a member extending radially from an inner surface of each arm, wherein each member comprises a ramp surface, an engagement surface extending transversely to the ramp surface, and an apex area that transitions between the ramp surface and the engagement surface.

Some embodiments provide when the priming device is in a priming-ready configuration, the male luer connector is partially inserted into the sleeve and the engagement surface of a member engages a bottom-facing edge of the male luer connector. Certain aspects provide when the priming device is in a priming configuration, each arm flexes away from the axis such that a cross-sectional width between the apex areas is at least equal to the outer surface of the male luer connector. In certain instances of the present disclosure, the inlet port is advanced over a portion of a male luer connector stem to fluidly couple the housing with the male luer connector, thereby opening the valve and creating a fluid pathway between the male luer connector and the chamber. In some instances, a hydrophobic filter is disposed in the opening.

In certain embodiments of the present disclosure, the opening extends through a portion of the housing opposite the inlet port. In some instances, the open first end of the sleeve has an inner cross-sectional width configured to receive an outlet port of the male luer connector.

In certain embodiments of the present disclosure, the inner cross-sectional width of the first end is equal to an outer cross-sectional width of the outlet port such that the outlet port is press fit into the sleeve partially toward the second end of the sleeve.

Some embodiments provide that when the priming device is in a priming-ready configuration, the engagement surface of each member contacts an edge of the outlet port to prevent insertion of the male luer connector beyond the member.

In certain embodiments of the present disclosure, the male luer connector comprises: an inlet port, an outlet port, and a body between the inlet port and the outlet port; a luer portion extending from within the body toward the outlet port, wherein a fluid path extends from the inlet port through the body and luer portion; and a post extending through the fluid path in the luer portion. In certain aspects, in a closed position, the post seals an open tip of the luer portion thereby closing the fluid path; and in an open position, the post is retracted toward the inlet port of the male luer connector and into the luer portion, thereby opening the fluid path.

Some embodiments provide that the inlet port defined in the housing has a thread extending circumferentially outward from an outer surface thereof, the thread configured to engage a mating thread on an inner surface of the outlet port to threadably couple the housing with the male luer connector.

In certain embodiments of the present disclosure, an outer surface of the housing comprises one or more channels between the second end of the sleeve and the opening to increase rigidity of the priming device, and provide increased torsional leverage when coupling or decoupling the sleeve with the male luer connector.

In certain embodiments of the present disclosure, the priming device further includes one or more ribs extending along an outer surface of the housing between the second end of the sleeve and the opening to increase rigidity of the priming device, and provide increased torsional leverage when coupling or decoupling the sleeve with the male luer connector.

An aspect of the present disclosure provides a priming device comprising: a housing defining a chamber and an inlet port fluidly coupled to the chamber, the housing comprising an opening extending through a portion of the housing opposite the inlet port, the opening configured to permit a gas to exit the chamber; a sleeve having an open first end configured to couple with a male luer connector, a second end coupled to the housing; and at least one window defined through the sleeve, the at least one window comprising an arm extending toward the first end and the arm including at least one member extending radially from an inner surface of each arm.

In certain embodiments of the present disclosure, an axis is defined between the first end and the second end of the sleeve and when the priming device is in a priming configuration, each arm flexes away from the axis such that a cross-sectional width between the apex areas is at least equal to the outer surface of the male luer connector.

Some embodiments provide that when the priming device is in a priming-ready configuration, the male luer connector is partially inserted into the sleeve and the engagement surface of the member engages a bottom-facing edge of the male luer connector.

In certain embodiments of the present disclosure, an axis is defined between the first end and the second end of the sleeve and when the priming device is in a priming configuration, each arm flexes away from the axis such that a cross-sectional width between the apex areas is at least equal to the outer surface of the male luer connector.

In certain embodiments of the present disclosure, the priming device further includes one or more ribs extending along an outer surface of the housing between the second end of the sleeve and the opening to increase rigidity of the priming device, and provide increased torsional leverage when coupling or decoupling the sleeve with the male luer connector.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Figure 1:
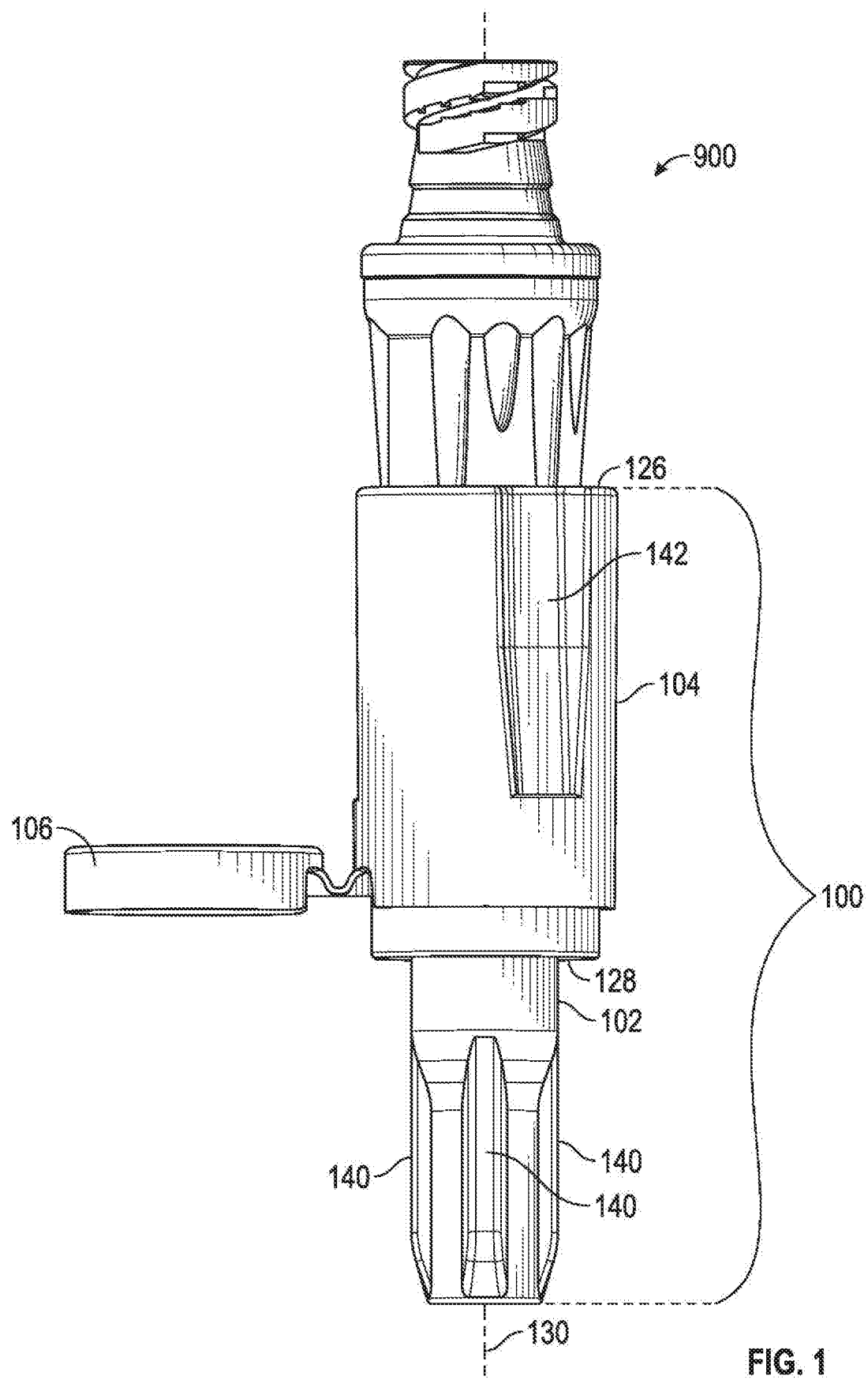
FIG. 1 illustrates a front view of a luer connector and embodiments of a priming device in accordance with aspects of the present disclosure.

Referring now to FIG. 1, a medical connector 900 and an embodiment of a priming device 100 in accordance with aspects of the present disclosure are illustrated. The priming device 100 comprises a housing 102 and a cover body 104, the cover body 104 interconnecting the housing 102 with the medical connector 900. In some embodiments, the cover body 104 comprises a lid 106. After the medical connector 900 is primed into the housing 102, the housing 102 may be decoupled from the cover body 104, and the cover body 104 enclosed by the lid 106 to prevent contamination of the medical connector 900.

Figure 2A:
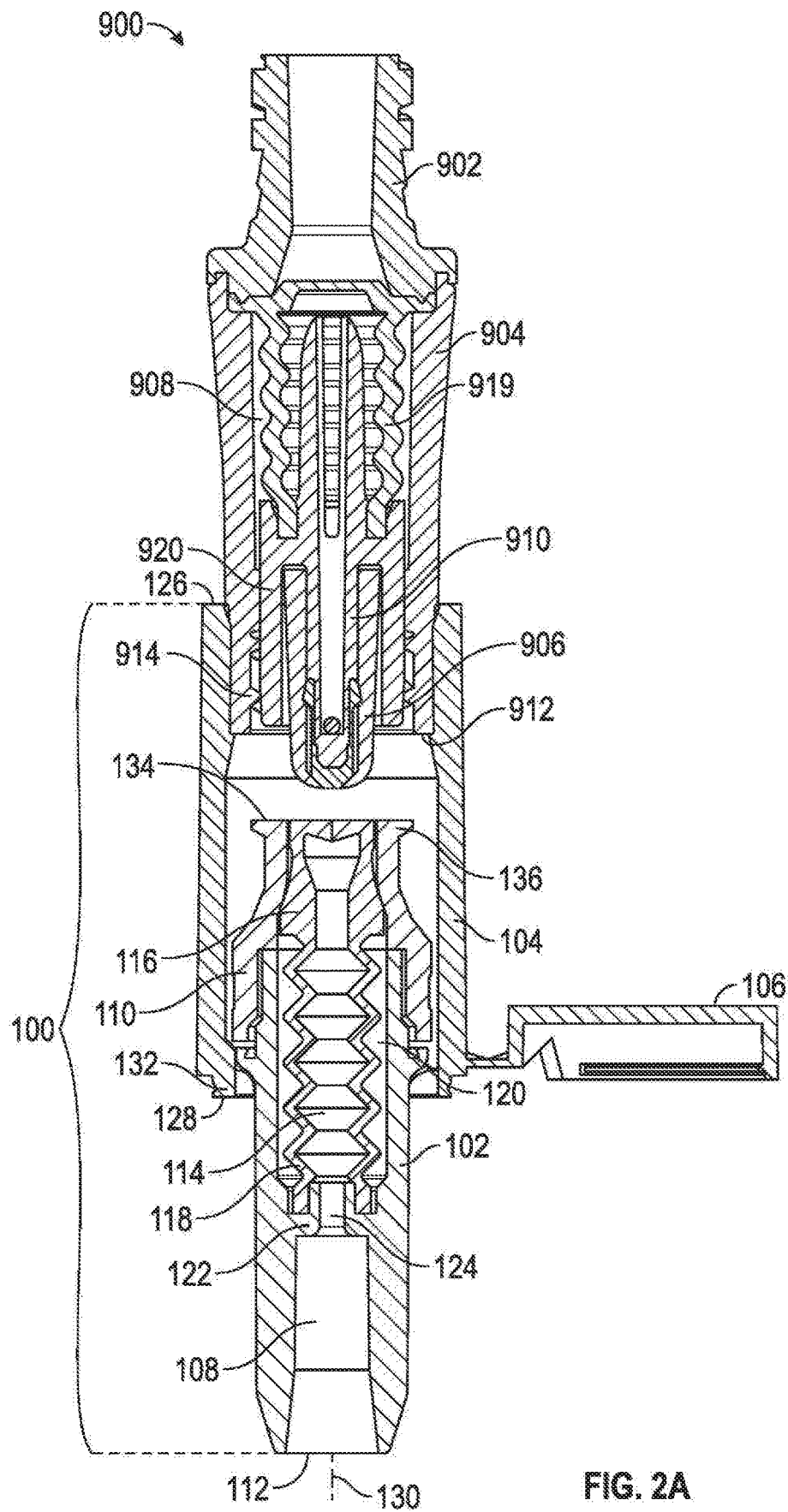
FIG. 2A illustrates a front sectional view of the luer connector and the priming device of FIG. 1 in a priming-ready configuration.

Referring to FIG. 2A, the priming device 100 of FIG. 1 is illustrated in a priming-ready configuration. For the purposes of illustration, the medical connector 900 is illustrated as a male Luer connector having an inlet port 902, an outlet port 912, and a body 904 between the inlet port 902 and the outlet port 912. A luer portion 906 extends from within the body 904 toward the outlet port 912. A fluid path 908 extends from the inlet port 902, through the body 904, and Luer portion 906. A post 910 extends through the fluid path in the Luer portion 906 when the medical connector 900 is in a closed position. In the closed position, the post 910 seals an open tip of the Luer portion 906 thereby closing the fluid path 908. A resilient bellows 919 extends between the inlet port 902 and the post 910. In some embodiments, elongate member 920, which may be an elongate cylindrical assembly or fingers, is connected to the post 910 and extends along an exterior of the Luer portion 906 toward the outlet port 912. When the medical connector 900 is in an open position, the elongate member 920 is engaged and retracted within the body 904 such that the bellows 919 are compressed between the elongate member 920 and the inlet port 902 and the post 910 is retracted toward the inlet port 902 and into the Luer portion 906, thereby opening the fluid path 908.

The housing 102 defines a chamber 108 and inlet port 110, wherein the chamber 108 and the inlet port 110 are fluidly coupled within the housing 102. The housing 102 further defines an opening 112 extending from within the chamber 108 to outside of the housing 102. In some embodiments, the opening 112 extends through a portion of the housing 102 opposite the inlet port 110. The opening 112 permits a gas to exit the chamber 108. A filter (not shown) is disposed in the opening 112. In some embodiments, the filter is a hydrophobic filter to permit gases to exit the chamber 108 when priming device 100 is utilized to prime the medical connector 900.

A valve 114 is disposed within the housing 102 and extends from the inlet port 110 toward the chamber 108. In some embodiments, the valve 114 defines a fluid pathway and, in an embodiment, includes a head portion 116 and a bellows portion 118. In a sealed position, illustrated in FIG. 2A, the valve 114 seals the inlet port 110. In an open position, illustrated in FIG. 2B, the valve 114 does not seal the inlet port 110.

In some embodiments, the chamber 108 is separated from the passage 120 by a chamber inlet 122 between the inlet port 110 and the opening 112. The chamber inlet 122 extends radially inward from an inner surface of the housing 102 to separate the passage 120 from the chamber 108 and to form an orifice or lumen 124 that fluidly connects the passage 120 to the chamber 108. In an embodiment, the chamber inlet 122 extends partially into the bellows portion 118 of the valve 114 so that a portion of the bellows is seated between the inner surface of the housing 102 and an outer surface of the chamber inlet 122. In some embodiments, the valve 114 is coupled to the chamber inlet 122 where the chamber inlet 122 extends into the bellows to provide a sealed interface between the valve 114 and the chamber inlet 122. In the priming-ready configuration (i.e., when the bellows portion 118 is extended), the head portion 116 extends into the inlet port 110 to provide a sealed interface between the valve 114 and the inlet port 110.

In the priming-ready configuration illustrated in FIG. 2A, the cover body 104 interconnects the housing 102 with the medical connector 900. The cover body 104 comprises an open first end 126, an open second end 128, and an axis 130 between the first end 126 and the second end 128. In the priming-ready configuration, the outlet port 912 of the medical connector 900 and the inlet port 110 of the housing 102 are coupled to the cover body 104 and aligned along the axis 130. However, the fluid path 908 of the medical connector 900, and the passage 120 of the housing 102, remain sealed.

In some embodiments, the cover body 104 is cylindrically shaped between the first end 126 and the second end 128. The first end 126 comprises an inner cross-sectional width that is configured to receive the outlet port 912. In some embodiments, the inner cross-sectional width of the first end 126 is equal to the outer cross-sectional width of the outlet port 912 such that the outlet port 912 is press fit into the cover body 104 partially toward the second end 128.

The second end 128 comprises an inner cross-sectional width configured to receive the inlet port 110 partially toward the first end 126. In some embodiments, the cover body 104 comprises one or more protrusion 132 extending axially inward from an inner surface of the cover body 104 at the second end 128. The protrusion 132 has an inner surface defining an inner cross-sectional width. The inner cross-sectional width of the protrusion 132 is less than the outer cross-sectional width of the inlet port 110. In some embodiments, the protrusion 132 is one or more flexible tabs. The flexible tabs yield to permit the inlet port 110 to be advanced toward the first end 126. A portion of the housing 102 having an outer cross-sectional width that is less than the outer cross-sectional width of the inlet port 110 allows the tabs to retain the inlet port 110 between the tabs and the first end 126 in the priming-ready configuration.

Figure 2B:
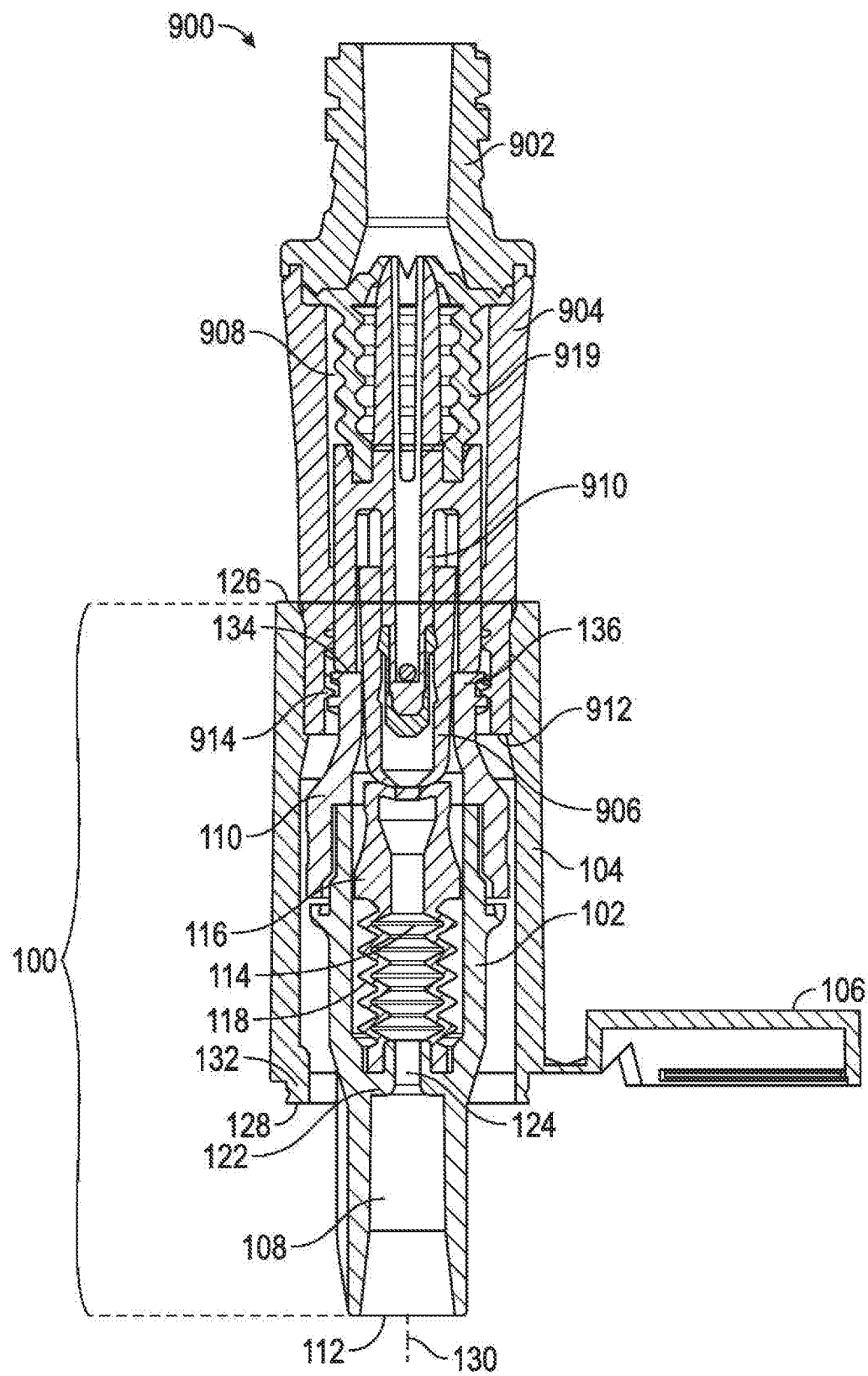
FIG. 2B illustrates a front sectional view of the luer connector and the priming device of FIG. 1 in a priming configuration.

In the priming configuration illustrated in FIG. 2B, the outlet port 912 of the medical connector 900 and the inlet port 110 of the housing 102 are coupled together and remain within the cover body 104. In the priming configuration, a fluid pathway is opened between the fluid path 908 of the medical connector 900 and the passage 120 of the housing 102.

To place the priming device 100 in a priming configuration, the medical connector 900 is moved toward the housing 102 such that the Luer portion 906 is advanced into the inlet port 110 to fluidly couple the medical connector 900 with the housing 102, thereby opening the valve 114 and creating a fluid pathway between the medical connector 900 and the chamber 108. In some embodiments, when the Luer portion 906 is advanced toward the inlet port 110, a top surface 134 of the inlet port 110 engages the elongate member 920 to compress the bellows 919 and urge the post 910 toward the inlet port 902 and thereby open the fluid path 908. As the Luer portion 906 is advanced into the inlet port 110, the Luer portion 906 is received into the passage 120 to unseal the inlet port 110. In some embodiments, the Luer portion 906 urges the head portion 116 of the valve 114 toward the chamber inlet 122 thereby causing the bellows portion 118 to fold and the fluid pathway through the valve 114 to open.

In some embodiments, a thread 136 extends circumferentially outward from an outer surface of the inlet port 110. As the medical connector 900 and housing 102 are moved toward each other and rotated about the axis 130, the thread 136 engages a mating thread 914 on an inner surface of the outlet port 912 to threadably couple the housing 102 with the medical connector 900.

In the priming configuration, a system coupled to the medical connector 900 is primed by transferring gasses from the system, through the medical connector 900, and into the chamber 108 of the priming device 100. As the gases are transferred through the fluid pathway and into the chamber 108, the gasses are permitted to exit the chamber 108 through the opening 112. In some embodiments, the gasses are caused to be transferred into the priming device 100 by forcing a fluid and a gas in the system into the priming device 100. A hydrophobic filter disposed in the opening 112 allows the gases to exit the housing 102 while retaining the fluid in the chamber 108, permitting the priming device 100 to be used in any orientation.

Figure 3:
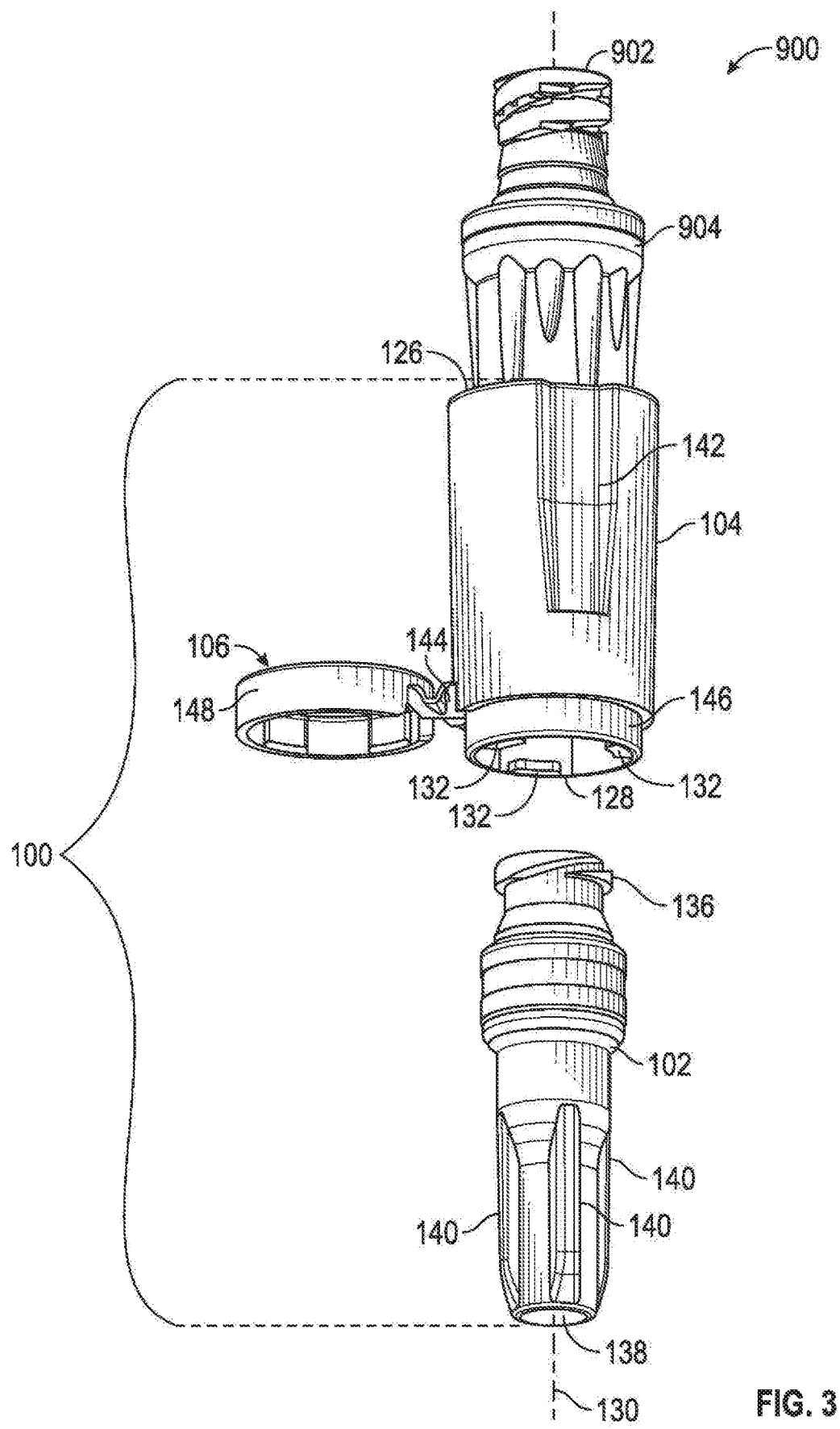
FIG. 3 illustrates a front perspective view of the luer connector and the priming device of FIG. 1 in a post-priming configuration in accordance with aspects of the present disclosure.

Referring to FIG. 3, a priming device 100 is illustrated in a post-priming configuration. In the post-priming configuration, the housing 102 is decoupled from the cover body 104, while the cover body 104 remains coupled to the medical connector 900. The priming device 100 is decoupled from the cover body 104 by overriding the tabs 132 (in FIG. 3, the feature where 102 is pointing to, is actually doing the overriding), and moving the priming device 100 away from the first end 126. In some embodiments, one or more rib 140 extends along the outer surface of the housing 102. Alternatively, the outer surface of the housing 102 comprises one or more channel between the second end 128 and the opening 112. In some embodiments, rib 140 extends along a portion of the outer surface of the housing 102 from the chamber inlet 122 to the opening 112. In some embodiments, one or more channel 142 extends along the outer surface of the cover body 104. Alternatively, the outer surface of the cover body 104 comprises one or more rib. Each of the rib 140 and the channel 142 increase the rigidity of the housing 102 and cover body 104, and provide increased torsional leverage when coupling, decoupling, or rotating either of the housing 102 and cover body 104 about the axis 130.

Figure 4:
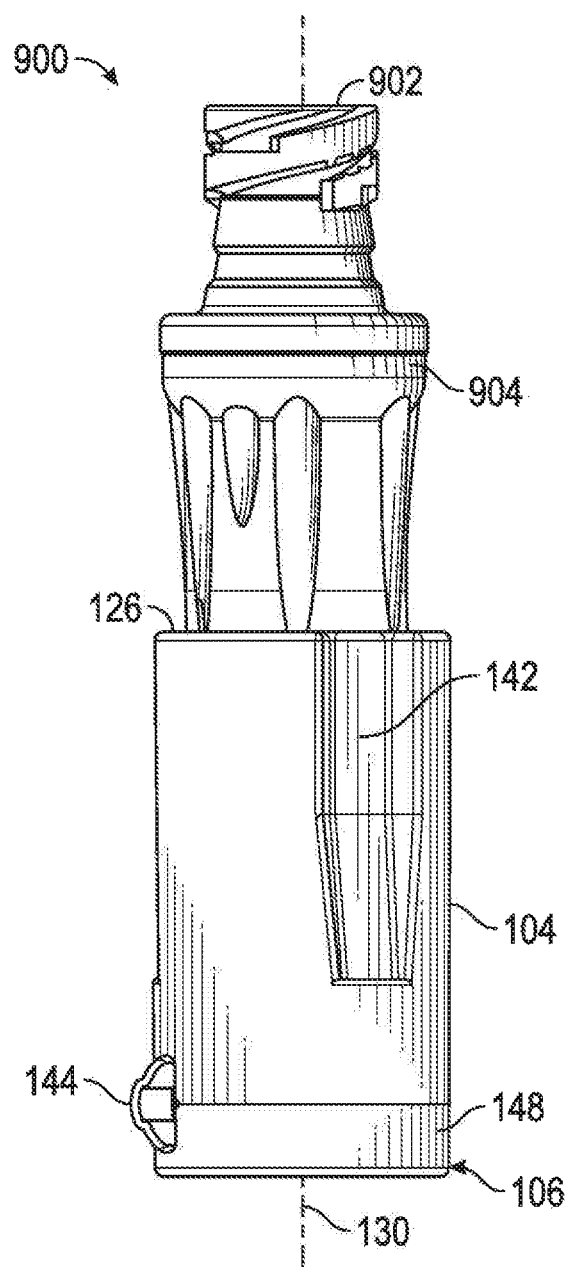
FIG. 4 illustrates a front view of the luer connector and the priming device of FIG. 1 in a post-priming configuration in accordance with aspects of the present disclosure.

Still referring to FIG. 3, the lid 106 is coupled to the cover body 104. In some embodiments, the lid 106 is rotatably coupled to the second end 128 of the cover body 104 by a hinge 144. In some embodiments, the hinge 144 is a living hinge. After the housing 102 is decoupled from the cover body 104, the lid 106 is rotated about hinge 144 to cover the second 128 as best illustrated in FIG. 4. In some embodiments, a portion 146 of the outer surface of the cover body 104 extending from the second end 128 comprises a reduced cross-sectional width. When the lid 106 is rotated to cover the second end 128, the portion 146 of the outer surface 148 of the cover body 104 having a reduced cross-sectional width is received into the lid 106 such that the outer surface of the lid is flush with the outer surface of the cover body 104.

Figure 5:
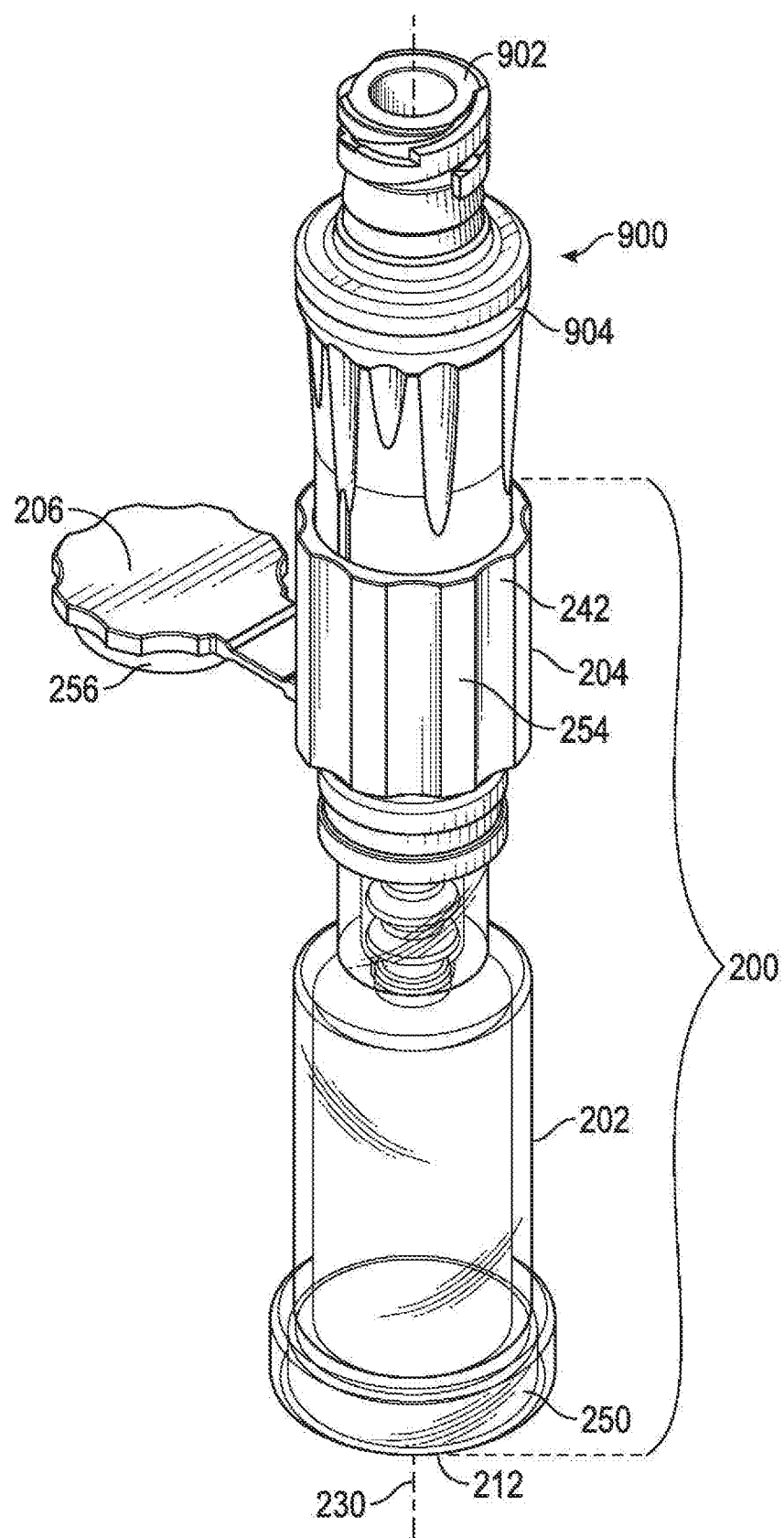
FIG. 5 illustrates a front perspective view of a luer connector and embodiments of a priming device in accordance with aspects of the present disclosure.
Figure 6:
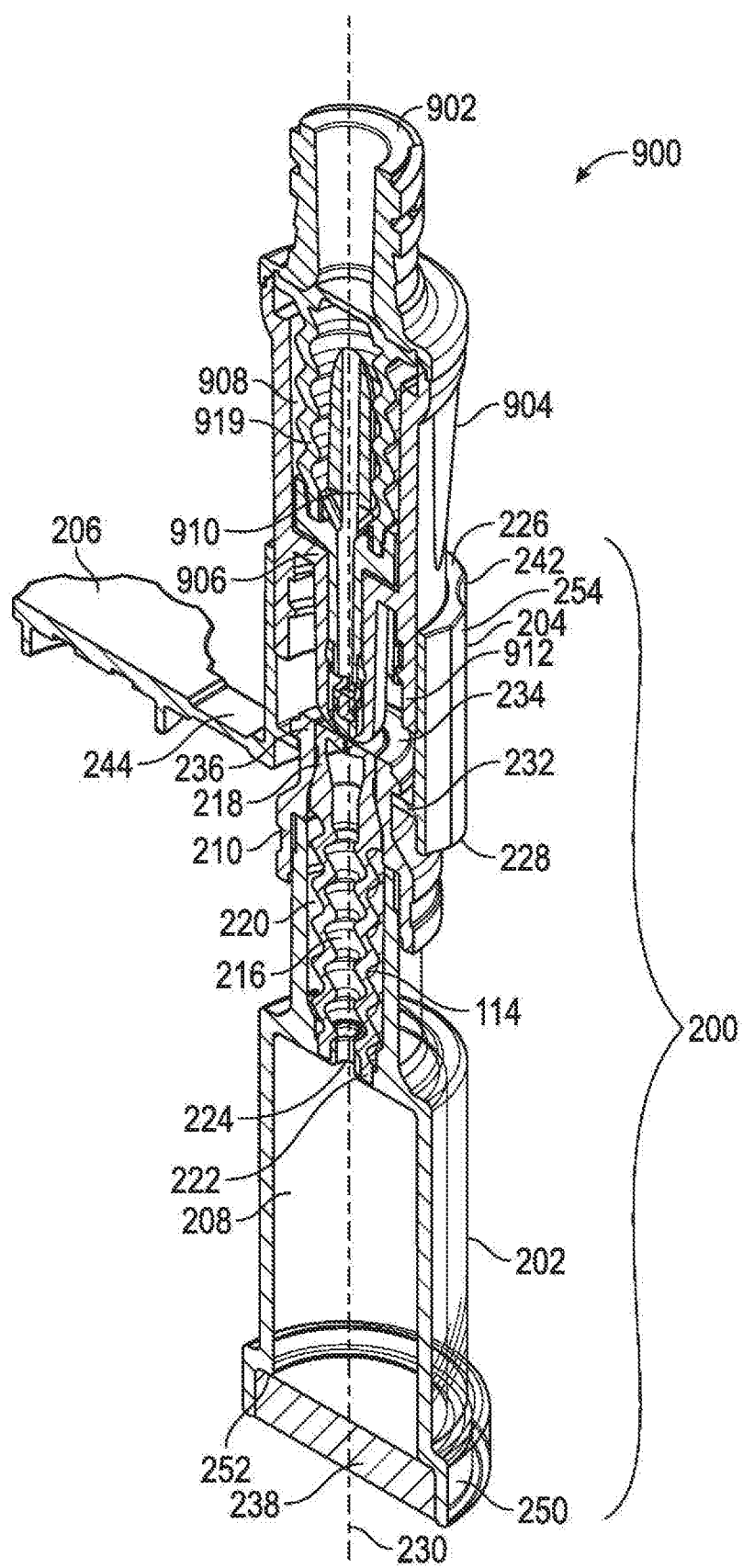
FIG. 6 illustrates a front sectional view of the luer connector and the priming device of FIG. 5 in a priming-ready configuration.

Referring now to FIGS. 5-6, a medical connector 900 and some embodiments of a priming device 200 in accordance with aspects of the present disclosure are illustrated. The priming device 200 comprises a housing 202 and a cover body 204, the cover body 204 interconnecting the housing 202 with the medical connector 900. In some embodiments, the cover body 204 comprises a lid 206. After the medical connector 900 is primed into the housing 202, the housing 202 may be decoupled from the cover body 204, and the cover body 204 enclosed by the lid 206 to prevent contamination of the medical connector 900.

Referring to FIG. 6, the priming device 200 is illustrated in a priming-ready configuration. For the purposes of illustration, the medical connector 900 is illustrated as a male Luer connector having an inlet port 902, an outlet port 912, and a body 904 between the inlet port 902 and the outlet port 912. A luer portion 906 extends from within the body 904 toward the outlet port 912. A fluid path 908 extends from the inlet port 902, through the body 904, and Luer portion 906. A post 910 extends through the fluid path in the Luer portion 906 when the medical connector 900 is in a closed position. In the closed position, the post 910 seals an open tip of the Luer portion 906 thereby closing the fluid path 908. A resilient bellows 919 extends between the inlet port 902 and the post 910. In some embodiments, elongate member 920 (not visible in FIG. 6) is connected to the post 910 and extends along an exterior of the Luer portion 906 toward the outlet port 912. When the medical connector 900 is in an open position, the bellows 919 is compressed and the post 910 is retracted toward the inlet port 902 and into the Luer portion 906 thereby opening the fluid path 908.

The housing 202 defines a chamber 208 and inlet port 210, wherein the chamber 208 and the inlet port 210 are fluidly coupled within the housing 202. The housing 202 further defines an opening 212 extending from within the chamber 208 to outside of the housing 202. In some embodiments, the opening 212 extends through a portion of the housing 202 opposite the inlet port 210. The opening 212 permits a gas to exit the chamber 208. A filter 238 is disposed in the opening 212. In some embodiments, the filter is a hydrophobic filter to permit gases to exit the chamber 208 when priming device 200 is utilized to prime the medical connector 900.

A valve 214 is disposed within the housing 202 and extends from the inlet port 210 toward the chamber 208. In some embodiments, the valve 214 defines a fluid pathway and, in some embodiments, includes a head portion 218 and a bellows portion 218. In a sealed position, illustrated in FIG. 6 the valve 214 seals the inlet port 210. In an open position (not shown) the valve 214 does not seal the inlet port 210.

The chamber 208 is separated from the passage 220 by a chamber inlet 222 between the inlet port 210 and the opening 212. The chamber inlet 222 extends radially inward from an inner surface of the housing 202 to separate the passage 220 from the chamber 208 and to form an orifice or lumen 224 that fluidly connects the passage 220 to the chamber 208. In some embodiments, the chamber inlet 222 extends partially into the bellows portion 216 of the valve 214 so that a portion of the bellows is seated between the inner surface of the housing 102 and an outer surface of the chamber inlet 222. In some embodiments the valve 214 is coupled to the chamber inlet 222 where the chamber inlet 222 extends into the bellows to provide a sealed interface between the valve 214 and the chamber inlet 222. In the priming-ready configuration (i.e., when the bellows portion 218 is extended), the head portion 218 extends into the inlet port 210 to provide a sealed interface between the valve 214 and the inlet port 210.

The outer surface of the chamber 208 comprises cross-sectional width that is greater than the outer cross-sectional width of the passage 220. The outer surface of the housing 202 defining the opening 212 comprises a larger outer cross-sectional width than the chamber 208, and forms an outer ridge 250. A ledge 252 is formed between the inside surface of the ridge 250 and the chamber 208. The outer cross-sectional width of the filter 238 is greater than or equal to the inside cross-sectional width of the ridge 250, allowing the filtered 238 to be seated in the opening 212. When seated in the opening 212, the ledge 252 prevents the filter 238 from shifting toward the chamber 208.

The cover body 204 interconnects the housing 202 with the medical connector 900. The cover body 204 comprises an open first end 226, an open second end 228, and an axis 230 between the first end 226 and the second end 228. In the priming ready configuration, the outlet port 912 of the medical connector 900 and the inlet port 210 of the housing 202 are coupled to the cover body 204 and aligned along the axis 230. In the priming-ready configuration, the fluid path 908 of the medical connector 200, and the passage 220 of the housing 202, remain sealed.

The cover body 204 is cylindrically shaped between the first end 226 and the second end 228. The first end 226 comprises an inner cross-sectional width that is configured to receive the outlet port 912 of the medical connector 900. In some embodiments, the inner cross-sectional width of the first end 226 is equal to the outer cross-sectional width of the outlet port 912 such that the outlet port 912 is press fit into the cover body 204 partially toward the second end 228.

The second end 228 comprises an inner cross-sectional width configured to receive the inlet port 210 partially toward the first end 226. In some embodiments, the cover body 204 comprises one or more protrusion 232 extending axially inward from an inner surface of the cover body 204 at the second end 228. The protrusion 232 has an inner surface defining an inner cross-sectional width. The inner cross-sectional width of the protrusion 232 is less than the outer cross-sectional width of the inlet port 210. In some embodiments, the protrusion 232 is one or more flexible tabs. The flexible tabs yield to permit the inlet port 210 to be advanced toward the first end 226. A portion of the housing 202 having an outer cross-sectional width that is less than the outer cross-sectional width of the inlet port 210 allows the tabs to retain the inlet port 200 between the tabs and the first end 226 in the priming-ready configuration.

To place the priming device 200 in a priming configuration, the medical connector 900 is moved toward the housing 202 such that the Luer portion 906 is advanced into the inlet port 210 to fluidly couple the housing 202 with the medical connector 900, thereby opening the valve 214 and creating a fluid pathway between the medical connector 900 and the chamber 208. In some embodiments, when the Luer portion 906 is advanced toward the inlet port 210, a top surface 234 of the inlet port 210 engages the elongate member 920 to urge the post 910 toward the inlet port 902 and thereby open the path 908. As the Luer portion 906 is advanced into the inlet port 210, the Luer portion 906 is received into the passage 220 to unseal the inlet port 210. In some embodiments, the Luer portion 906 urges the head portion 218 of the valve 214 toward the chamber inlet 222 thereby causing the bellows portion 218 to fold and the valve 214 to open.

A thread 236 extends circumferentially outward from an outer surface of the inlet port 210. As the medical connector 900 is moved toward the housing 202 and rotated about the axis 230, the thread 236 engages a mating thread 914 on an inner surface of the outlet port 912 to threadably couple the housing 202 with the medical connector 900.

In the priming configuration, a system coupled to the medical connector 900 is primed by transferring gasses from the system, through the medical connector 900, and into the chamber 208 of the priming device 200. As the gases are transferred through the fluid pathway and into the chamber 208, the gasses are permitted to exit the chamber 208 through the opening 212. In some embodiments, the gasses are caused to be transferred into the priming device 200 by forcing a fluid in the system into the priming device 200. Where the filter 238 is a hydrophobic filter, the filter 238 disposed in the opening 212 allows the gases to exit the housing 202 while retaining the fluid in the chamber 208, permitting the priming device 200 to be used in any orientation.

In a post-priming configuration, the housing 202 is decoupled from the cover body 204, while the cover body 204 remains coupled to the medical connector 900. The priming device 200 is decoupled from the cover body 204 by unscrewing the threads 236 of the inlet port 210 from the threads 914 of the medical connector 900, and moving the priming device 200 away from the first end 226. One or more channels 242 extend along the outer surface of the cover body 204. In some embodiments, one or more channels 242 and ribs 254 alternate around the outer surface of the cover body 204. Each of the rib 254 and the channel 242 increase the rigidity of the cover body 204, and provide increased torsional leverage when coupling, decoupling, or rotating either of the housing 202 and cover body 204 about the axis 230.

A lid 206 is rotatably coupled to the second end 228 of the cover body 204 by a hinge 244. In some embodiments, the hinge 244 is a living hinge, meaning that a flexible material is used to couple the adjoining pieces and that the material flexes or deforms to provide relative rotational movement instead of separate component that slide relatively at the hinge. In some embodiments, a portion 256 of the lid 206 has a cross-sectional width equal to the inner cross sectional width of the second end 228 of the cover body 204. After the housing 202 is decoupled from the cover body 204, the lid 206 is rotated about hinge 244 such that the portion 256 of the lid 206 having a reduced cross-sectional width is received into the second end 228 of the cover body 204 to cover the second 228.

Figure 7:
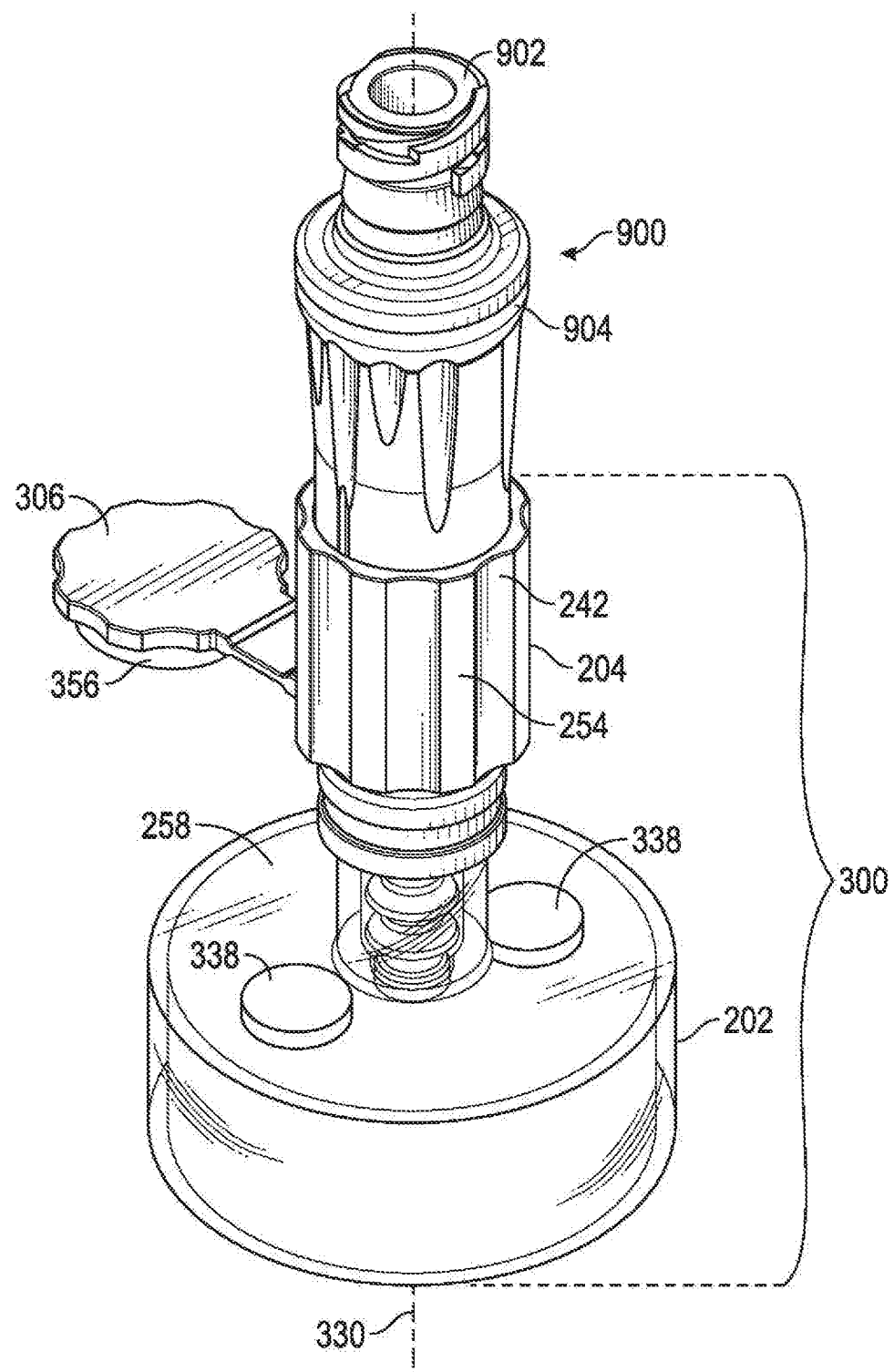
FIG. 7 illustrates a front perspective view of a luer connector and embodiments of a priming device in accordance with aspects of the present disclosure.
Figure 8:
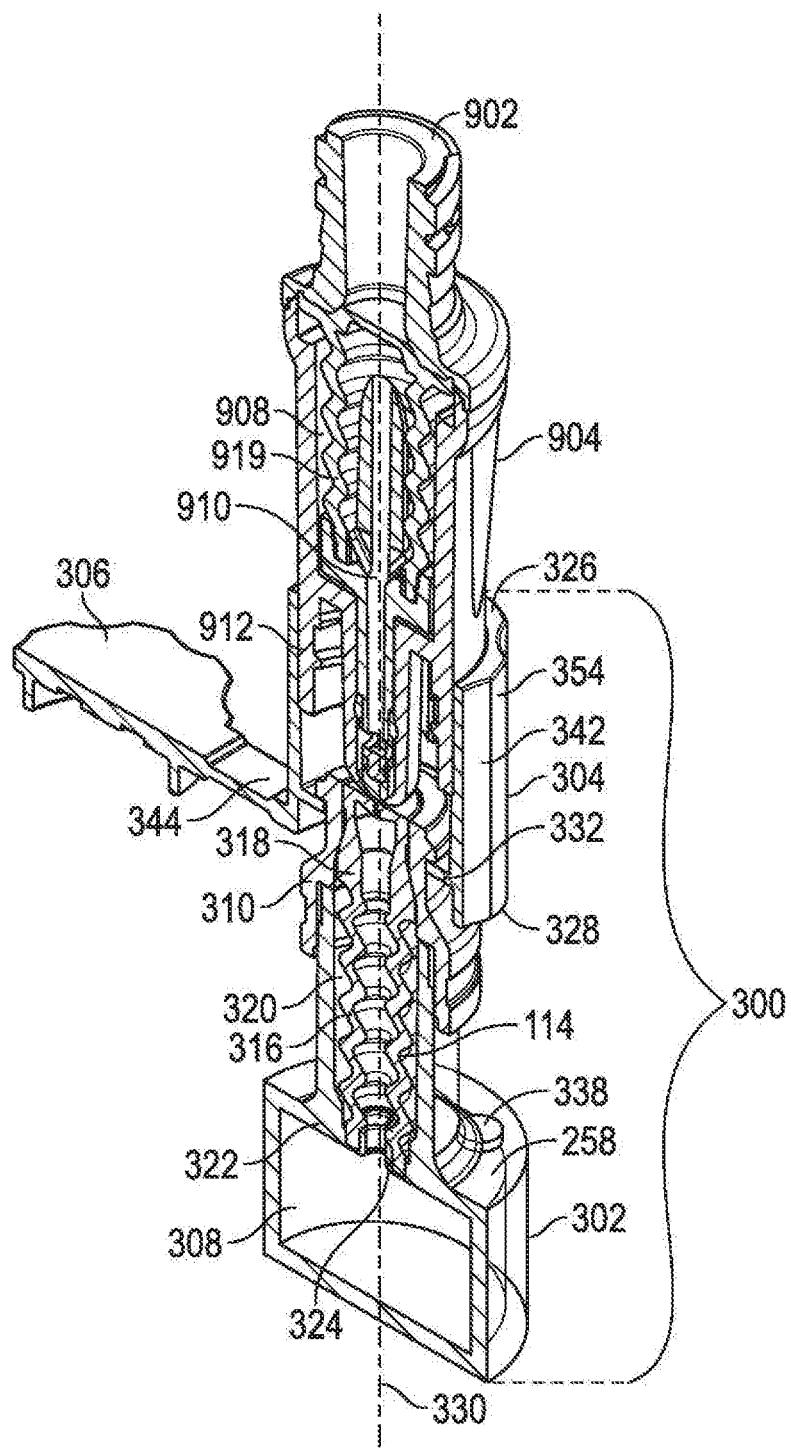
FIG. 8 illustrates a front sectional view of the luer connector and the priming device of FIG. 7 in a priming-ready configuration.

Referring now to FIGS. 7-8, a medical connector 900 and some embodiments of a priming device 300 in accordance with aspects of the present disclosure are illustrated. The priming device 300 comprises a housing 302 and a cover body 304, the cover body 304 interconnecting the housing 302 with the medical connector 900. In some embodiments, the cover body 304 comprises a lid 306. After the medical connector 900 is primed into the housing 302, the housing 302 may be decoupled from the cover body 304, and the cover body 304 enclosed by the lid 306 to prevent contamination of the medical connector 900.

Referring to FIG. 8, the priming device 300 is illustrated in a priming-ready configuration. For the purposes of illustration, the medical connector 900 is illustrated as a male Luer connector having an inlet port 902, an outlet port 912, and a body 904 between the inlet port 902 and the outlet port 912. A luer portion 906 extends from within the body 904 toward the outlet port 912. A fluid path 908 extends from the inlet port 902, through the body 904, and Luer portion 906. A post 910 extends through the fluid path in the Luer portion 906 when the medical connector 900 is in a closed position. In the closed position, the post 910 seals an open tip of the Luer portion 906 thereby closing the fluid path 908. A resilient bellows 919 extends between the inlet port 902 and the post 910. In some embodiments, elongate member 920 is connected to the post 910 and extends along an exterior of the Luer portion 906 toward the outlet port 912. When the medical connector 900 is in an open position, the post 910 is toward the inlet port 902 and into the Luer portion 906 thereby opening the fluid path 908.

The housing 302 defines a chamber 308 and an inlet port 310, wherein the chamber 308 and the inlet port 310 are fluidly coupled within the housing 302. The outer surface of the chamber 308 comprises cross-sectional width that is greater than the outer cross-sectional width of the passage 320. An outer surface of the housing 302, between the chamber 308 and the passage 320, includes a surface 258 extending circumferentially outward from an axis 330 defined between the chamber 308 and inlet port 310. An opening through the surface 258 extends from within the chamber 308 to outside of the housing 302. The opening 312 permits a gas to exit the chamber 308. A filter 338 is disposed in the opening 312. In some embodiments, the filter is a hydrophobic filter to permit gases to exit the chamber 308 when priming device 300 is utilized to prime the medical connector 900.

The cover body 304 interconnects the housing 302 with the medical connector 900. The cover body 304 comprises an open first end 326 and an open second end 328, with the axis 330 extending between the first end 326 and the second end 328. In the priming ready configuration, the outlet port 912 of the medical connector 900 and the inlet port 310 of the housing 302 are coupled to the cover body 304 and aligned along the axis 330. In the priming-ready configuration, the fluid path 908 of the medical connector 900, and the passage 320 of the housing 302, remain sealed.

The cover body 304 is cylindrically shaped between the first end 326 and the second end 328. The first end 326 comprises an inner cross-sectional width that is configured to receive the outlet port 912. In some embodiments, the inner cross-sectional width of the first end 326 is equal to the outer cross-sectional width of the outlet port 912 such that the outlet port 912 is press fit into the cover body 304 partially toward the second end 328.

The second end 328 comprises an inner cross-sectional width configured to receive the inlet port 310 partially toward the first end 326. In some embodiments, the cover body 304 comprises one or more protrusion 332 extending axially inward from an inner surface of the cover body 304 at the second end 328. The protrusion 332 has an inner surface defining an inner cross-sectional width. The inner cross-sectional width of the protrusion 332 is less than the outer cross-sectional width of the inlet port 310. In some embodiments, the protrusion 332 is one or more flexible tabs. The flexible tabs yield to permit the inlet port 310 to be advanced toward the first end 326. A portion of the housing 302 having an outer cross-sectional width that is less than the outer cross-sectional width of the inlet port 310 allows the tabs to retain the inlet port 300 between the tabs and the first end 326 in the priming-ready configuration.

To place the priming device 300 in a priming configuration, the medical connector 900 is moved toward the housing 302 such that the Luer portion 906 is advanced into the inlet port 310 to fluidly couple the housing 302 with the medical connector 900, thereby opening the valve 314 and creating a fluid pathway between the medical connector 900 and the chamber 308. In some embodiments, when the Luer portion 906 is advanced toward the inlet port 310, a top surface 334 of the inlet port 310 engages the elongate member 920 to urge the post 910 toward the inlet port 902 and thereby open the path 908. As the Luer portion 906 is advanced into the inlet port 310, the Luer portion 906 is received into the passage 320 to unseal the inlet port 310. In some embodiments, the Luer portion 906 urges the head portion 318 of the valve 314 toward the chamber inlet 322 thereby causing the bellows portion 316 to fold and the valve 314 to open.

A thread 336 extends circumferentially outward from an outer surface of the inlet port 310. As the medical connector 900 is moved toward the housing 302 and rotated about the axis 330, the thread 336 engages a mating thread 914 on an inner surface of the outlet port 912 to threadably couple the housing 302 with the medical connector 900.

In the priming configuration, a system coupled to the medical connector 900 is primed by transferring gasses from the system, through the medical connector 900, and into the chamber 308 of the priming device 300. Fluid and gasses from the system enter the chamber 308. Because the opening is located through the surface 258, above the chamber 308, the gasses are permitted to exit the chamber 308 through the opening in the surface 258 unobstructed by the fluid accumulating in the chamber 308. Where the filter 338 is a hydrophobic filter, the filter 338 disposed in the opening 312 allows the gases to exit the housing 302 while retaining the fluid in the chamber 308, permitting the priming device 300 to be used in any orientation.

In a post-priming configuration, the housing 302 is decoupled from the cover body 304, while the cover body 304 remains coupled to the medical connector 900. The priming device 300 is decoupled from the cover body 304 by unscrewing the threads 336 of the inlet port 310 from the threads 914 of the medical connector 900, and moving the priming device 300 away from the first end 326. One or more channels 342 extend along the outer surface of the cover body 304. In some embodiments, one or more channels 342 and ribs 354 alternate around the outer surface of the cover body 304. Each of the rib 354 and the channel 342 increase the rigidity of the cover body 304, and provide increased torsional leverage when coupling, decoupling, or rotating either of the housing 302 and cover body 304 about the axis 330.

A lid 306 is rotatably coupled to the second end 328 of the cover body 304 by a hinge 344. In some embodiments, the hinge 344 is a living hinge. In some embodiments, a portion 356 of the lid 306 has a cross-sectional width equal to the inner cross sectional width of the second end 328 of the cover body 304. After the housing 302 is decoupled from the cover body 304, the lid 306 is rotated about hinge 344 such that the portion 356 of the lid 306 having a reduced cross-sectional width is received into the second end 328 of the cover body 304 to cover the second 328.

Referring now to FIGS. 9A-12B, a medical connector 900 and some embodiments of a priming device 400 in accordance with aspects of the present disclosure are illustrated. The priming device 400 comprises a housing 402 and a sleeve 404, the sleeve 404 interconnecting the housing 402 with the medical connector 900. The sleeve 404 comprises an open first end 426, a closed second end 428 coupled the housing 402, and an axis 430 between the first end 426 and the second end 428. The sleeve 404 defines one or more window 460 through the sleeve 404. Each window 460 comprises an arm 462 extending from a bottom of each window, partially toward the first end 426 and parallel to the axis 430.

Figure 10:
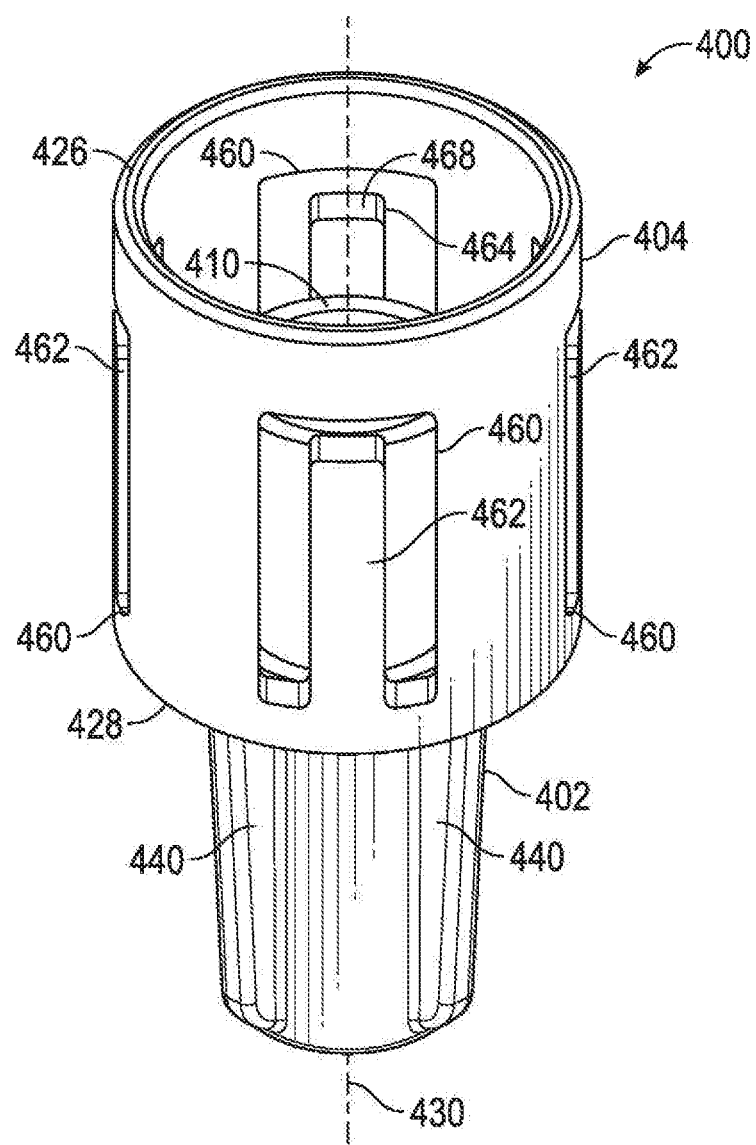
FIG. 10 illustrates a front perspective view of the priming device of FIG. 9.
Figure 11:
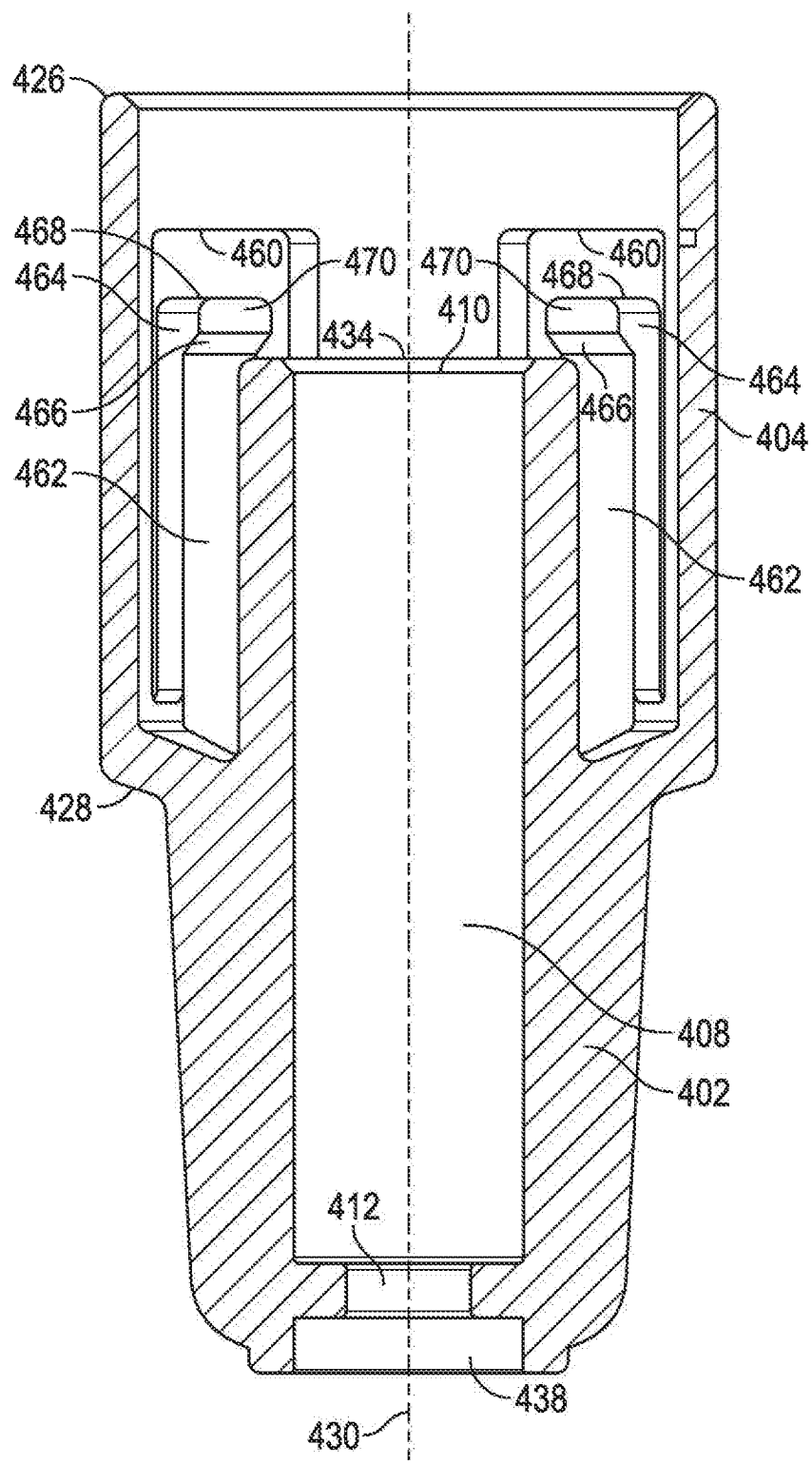
FIG. 11 illustrates a front sectional view of the priming device of FIG. 9.

Referring to FIGS. 10-11, the housing 402 defines a chamber 408 and inlet port 410, wherein the chamber 408 and the inlet port 410 are fluidly coupled within the housing 402. The housing 402 further defines an opening 412 extending from within the chamber 408 to outside of the housing 402. The opening 412 extends through a portion of the housing 402 opposite the inlet port 410. The opening 412 permits a gas to exit the chamber 408. A filter 438 is disposed in the opening 412. In some embodiments, the filter is a hydrophobic filter configured to permit gases to exit the chamber 408 when priming device 400 is utilized to prime the medical connector.

An end of each arm 462, opposite the bottom of each window, includes a member 464 extending radially from an inner surface of each arm 462 toward the axis 430. Each member 464 comprises a ramp surface 466, an engagement surface 468 extending transversely to the ramp surface 466, and an apex area 470 that transitions between the ramp surface and the engagement surface. In some embodiments, the engagement surface 468 is perpendicular to the axis 430.

Figure 12B:
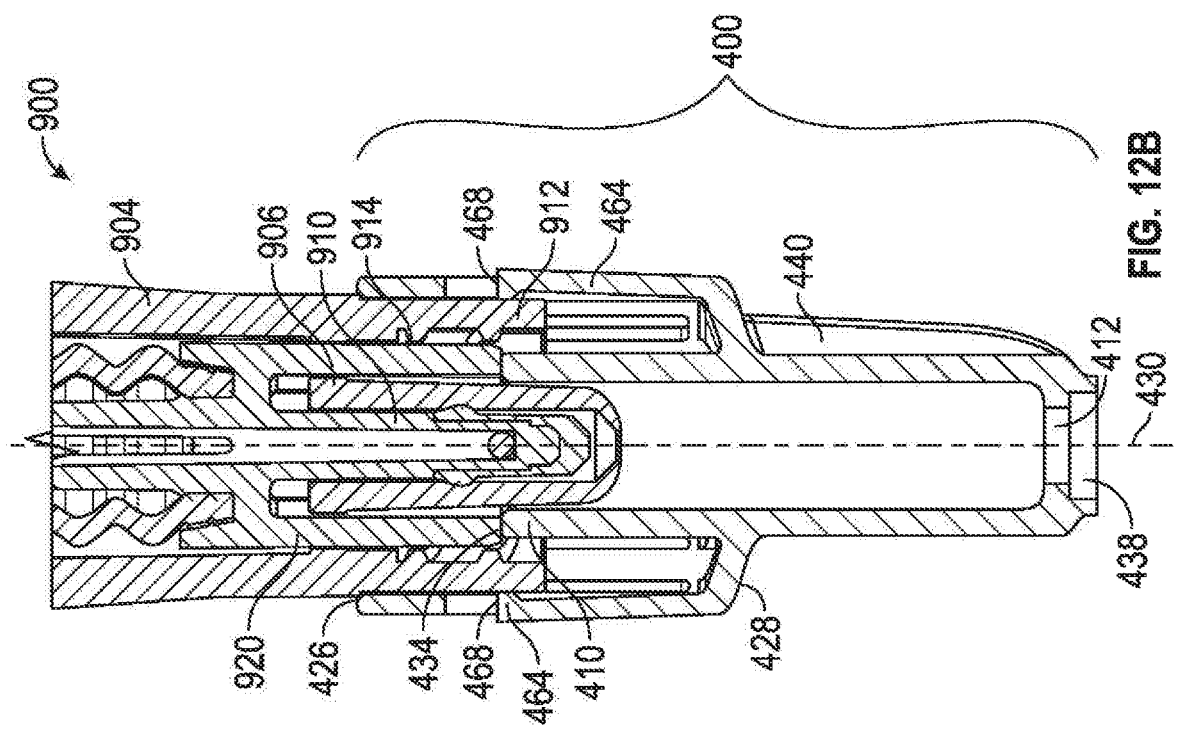
FIG. 12B illustrates a front sectional view of the luer connector and the priming device of FIG. 9 in a priming configuration.
Figure 12A:
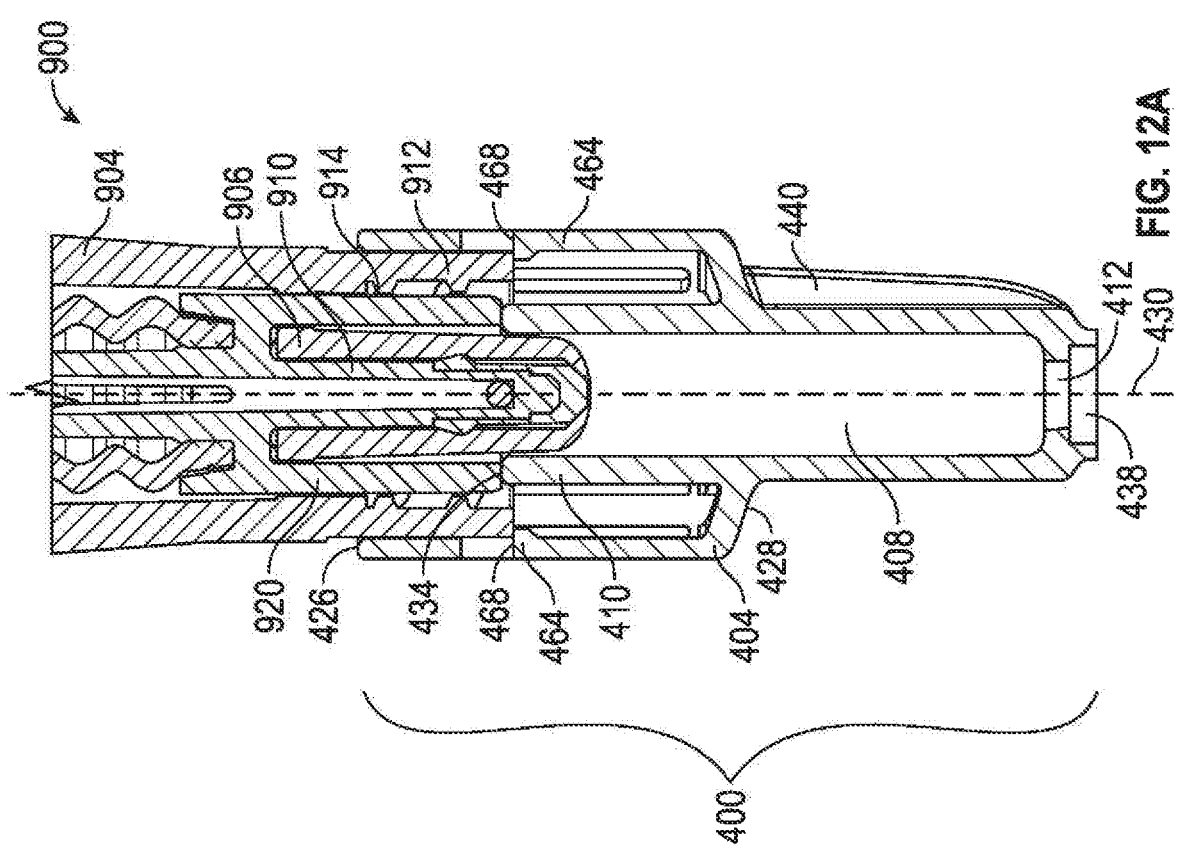
FIG. 12A illustrates a front sectional view of the luer connector and the priming device of FIG. 9 in a priming-ready configuration.

Referring to FIGS. 12A-12B, a portion of a medical connector 900 is illustrated coupled with the priming device 400. For the purposes of illustration, the medical connector 900 is illustrated as a male Luer connector having an inlet port (not shown), an outlet port 912, and a body 904 between the inlet port and the outlet port 912. A luer portion 906 extends from within the body 904 toward the outlet port 912. A fluid path extends from the inlet port 902, through the body 904, and Luer portion 906. A post 910 extends through the fluid path in the Luer portion 906 when the medical connector 900 is in a closed position. In the closed position, illustrated in FIG. 12A, the post 910 seals an open tip of the Luer portion 906 thereby closing the fluid path. In some embodiments, elongate member 920 is connected to the post 910 and extends along an exterior of the Luer portion 906 toward the outlet port 912. When the medical connector 900 is in an open position, illustrated in FIG. 12B, the post 910 is retracted toward the inlet port 902 and into the Luer portion 906 thereby opening the path 908.

The sleeve 404 is cylindrically shaped between the first end 426 and the second end 428. The first end 426 comprises an inner cross-sectional width that is configured to receive the outlet port 912. In some embodiments, the inner cross-sectional width of the first end 426 equal to the outer cross-sectional width of the outlet port 912 such that the outlet port 912 is press fit into the cover body 404 partially toward the second end 428. In the priming-ready configuration illustrated in FIGS. 9A and 12A, the engagement surface 468 of each arm 462 contacts an edge of the outlet port 912 to prevent insertion of the medical connector 900 beyond the member 464.

Figures 9A, 9B:
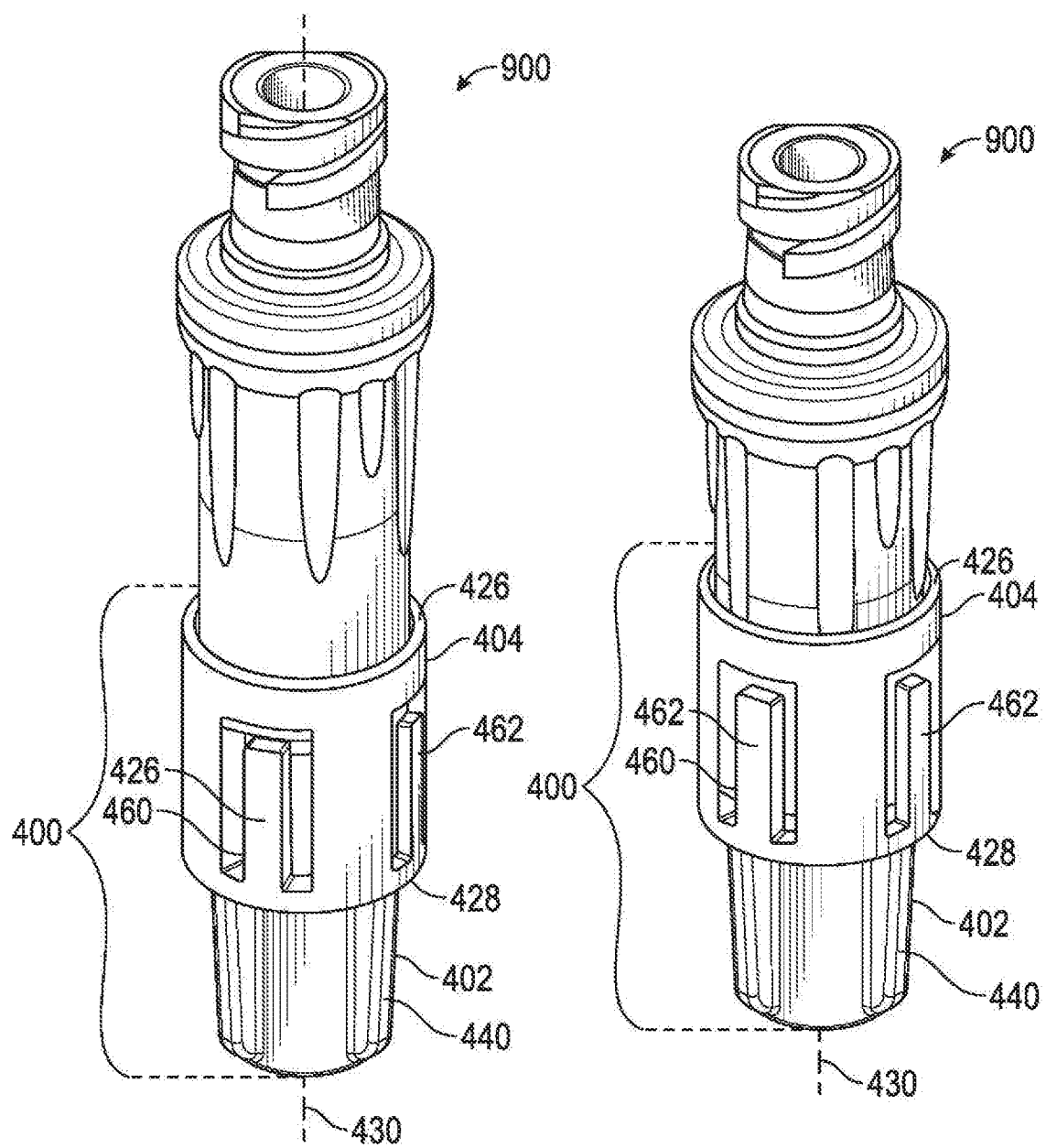
FIG. 9A illustrates a front view of a luer connector and embodiments of a priming device in a priming-ready configuration in accordance with aspects of the present disclosure.
FIG. 9B illustrates a front view of a luer connector and embodiments of a priming device in a priming configuration in accordance with aspects of the present disclosure.

To place the priming device 400 in a priming configuration illustrated in FIGS. 9B and 12B, the medical connector 900 is moved toward the priming device 400, causing the arms 462 to flex away from the axis 430 such that the cross-sectional width between the apex area 470 of each member 464 is greater than or equal to an outer surface of the body 904 at the outlet port 912. With each arm 462 deflected, the medical connector 900 is permitted to be inserted beyond the member 464 with the apex area 470 of each member 464 in contact with the outer surface of the body 904. As the medical connector 900 is moved toward the priming device 400, the Luer portion 906 is advanced over the inlet port 410 and a top surface 434 engages the elongate member 920. As the medical connector 900 is moved toward the priming device 400, the elongate member 920 and post 910 are retracted toward the inlet port 902 thereby creating a fluid pathway between the medical connector 900 and the chamber 408. In some embodiments, a valve is disposed within the housing 402 and extends from the inlet port 410 toward the chamber 408. As the Luer portion 906 is advanced into the inlet port 410, the Luer portion 906 is received into the passage 420 displace the valve and unseal the inlet port 410. In some embodiments, the valve includes a head portion and a bellows portion. As the Luer portion 906 is received into the passage 420, the head portion of the valve is urged toward the chamber thereby causing a bellows portion to fold and the valve to open.

In some embodiments, a thread (not shown) extends circumferentially outward from an outer surface of the inlet port 410. As the medical connector 900 is moved toward the housing 402 and rotated about the axis 430, the thread engages a mating thread 914 on an inner surface of the outlet port 912 to threadably couple the housing 402 with the medical connector 900.

In the priming configuration, a system coupled to the medical connector 900 is primed by transferring gasses from the system, through the medical connector 900, and into the chamber 408 of the priming device 400. As the gases are transferred through the fluid pathway and into the chamber 408, the gasses are permitted to exit the chamber 408 through the opening 412. In some embodiments, the gasses are caused to be transferred into the priming device 400 by forcing a fluid in the system into the priming device 400. Where the filter 438 is a hydrophobic filter, the filter 438 disposed in the opening 412 allows the gases to exit the housing 402 while retaining the fluid in the chamber 408, permitting the priming device 400 to be used in any orientation.

In some embodiments, one or more rib 440 extends along the outer surface of the housing 402 between the second end 428 and the opening 412. Alternatively, the outer surface of the housing 402 comprises one or more channel between the second end 428 and the opening 412. The ribs 440 or channels increase the rigidity of the priming device 400, and provide increased torsional leverage when coupling or decoupling priming device 400 with the medical connector 900.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A priming assembly comprising:
   a male luer connector comprising:
      an inlet port, an outlet port, and a body between the inlet port and the outlet port;
      a luer portion extending from within the body toward the outlet port, wherein a fluid path extends from the inlet port through the body and luer portion; and
      a post extending through the fluid path in the luer portion, wherein in a closed position, the post seals an open tip of the luer portion thereby closing the fluid path, and in an open position, the post is retracted toward the inlet port of the male luer connector and into the luer portion, thereby opening the fluid path; and
   a priming device comprising:
      a housing defining a chamber and an inlet port, wherein the chamber and the inlet port are fluidly coupled, the housing comprising an opening extending from within the chamber to outside the housing and configured to permit a gas to exit the chamber;
      a sleeve having an open first end configured to couple with the male luer connector, a second end coupled to the housing, and an axis between the first end and the second end, wherein the sleeve defines at least one window;
      an arm extending from a bottom of each window toward the first end, wherein two arms are positioned opposite one another; and
      a member extending radially from an inner surface of each arm, wherein each member comprises a ramp surface, an engagement surface extending transversely to the ramp surface, and an apex area that transitions between the ramp surface and the engagement surface,
   wherein when the priming device is in a priming-ready configuration with the male luer connector,
   the male luer connector is partially inserted into the sleeve and the engagement surface of each member contacts an edge of the outlet port of the male luer connector to prevent insertion of the male luer connector beyond the member, and
   each arm flexes away from the axis such that a cross-sectional width between the apex areas is at least equal to an outer surface of the male luer connector.

2. The priming device of claim 1, wherein the inlet port is advanced over a portion of a male luer connector stem of the male luer connector to fluidly couple the housing with the male luer connector, thereby creating a fluid pathway between the male luer connector and the chamber.

3. The priming device of claim 1, wherein a filter is disposed in the opening.

4. The priming device of claim 1, wherein the opening extends through a portion of the housing opposite the inlet port.

5. The priming device of claim 1, wherein the open first end of the sleeve has an inner cross-sectional width configured to receive the outlet port of the male luer connector.

6. The priming device of claim 1, wherein an outer surface of the housing comprises one or more channels between the second end of the sleeve and the opening to increase rigidity of the priming device, and provide increased torsional leverage when coupling or decoupling the sleeve with the male luer connector.

7. The priming device of claim 1, further comprising one or more ribs extending along an outer surface of the housing between the second end of the sleeve and the opening to increase rigidity of the priming device, and provide increased torsional leverage when coupling or decoupling the sleeve with the male luer connector.

8. The priming device of claim 3, wherein the filter comprises a hydrophobic filter.

9. The priming device of claim 5, wherein the inner cross-sectional width of the first end is equal to an outer cross-sectional width of the outlet port of the male luer connector such that the outlet port is press fit into the sleeve partially toward the second end of the sleeve.

10. A priming assembly comprising:
a male luer connector comprising:
an inlet port, an outlet port, and a body between the inlet port and the outlet port;
a luer portion extending from within the body toward the outlet port, wherein a fluid path extends from the inlet port through the body and luer portion; and
a post extending through the fluid path in the luer portion, wherein in a closed position, the post seals an open tip of the luer portion thereby closing the fluid path, and in an open position, the post is retracted toward the inlet port of the male luer connector and into the luer portion, thereby opening the fluid path; and
a priming device comprising:
a housing defining a chamber and an inlet port fluidly coupled to the chamber, the housing comprising an opening extending through a portion of the housing opposite the inlet port, the opening configured to permit a gas to exit the chamber;
a sleeve having an open first end configured to couple with the male luer connector, a second end coupled to the housing; and
at least one window defined through the sleeve, the at least one window comprising an arm extending toward the first end and the arm including at least one member extending radially from an inner surface of each arm,
wherein when the priming device is in a priming-ready configuration with the male luer connector,
the male luer connector is partially inserted into the sleeve and an engagement surface of each member engages a bottom-facing edge of the male luer connector to prevent insertion of the male luer connector beyond the member, and
two arms are positioned opposite one another and each arm flexes away from a longitudinal axis such that a cross-sectional width between the arms is at least equal to an outer surface of the male luer connector.

11. The priming device of claim 10, wherein each member comprises a ramp surface, the engagement surface extending transversely to the ramp surface, and an apex area that transitions between the ramp surface and the engagement surface.

12. The priming device of claim 10, further comprising one or more ribs extending along an outer surface of the housing between the second end of the sleeve and the opening to increase rigidity of the priming device, and provide increased torsional leverage when coupling or decoupling the sleeve with the male luer connector.

13. The priming device of claim 11, wherein the axis is defined between the first end and the second end of the sleeve, and wherein the cross-sectional width between the apex areas is at least equal to the outer surface of the male luer connector.

* * * * *